United States Patent [19]

Duffett

[11] Patent Number: Plant 6,051

[45] Date of Patent: Dec. 1, 1987

[54] CHRYSANTHEMUM PLANT NAMED CALVEX

[75] Inventor: William E. Duffett, Salinas, Calif.

[73] Assignee: Yoder Brothers, Inc., Barberton, Ohio

[21] Appl. No.: 786,000

[22] Filed: Oct. 10, 1985

[51] Int. Cl.[4] ..... A01H 5/00

[52] U.S. Cl. ..... Plt./79

[58] Field of Search ..... Plt./79

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Calvex particularly characterized as to uniqueness by the combined characteristics of flat capitulum form; decorative capitulum type; greyed-orange ray floret color; diameter across face of capitulum of up to 9 cm at maturity; uniform nine to ten week photoperiodic flowering response to short days; tall plant height when grown single stem; 20 to 25 cm peduncles on open, normally terminal sprays; and 13° C. minimum temperature tolerance for initiation and development of flowering buds with a 12 to 13 hour continuous dark period.

3 Drawing Figures

The present invention comprises a new and distinct cultivar of Chrysanthemum, botanically known as *Dentrenthema morifolium*, Ramat., previously *Chrysanthemum morifolium*, Ramat., and referred to by the cultivar name Calvex.

Calvex, identified as 79T30004, was originated from a cross made in a controlled breeding program in Salinas, Calif., in 1978.

The female parent of Calvex was the cultivar identified as Win, disclosed in U.S. Plant Pat. No. 5,108. The male parent of Calvex, identified as 78*97009, was an unnamed seedling.

Calvex was discovered and selected as one flowering plant within the progeny of the stated cross by William E. Duffett in October of 1980, in a controlled environment in Salinas, Calif.

The first act of asexual reproduction of Calvex was accomplished when vegetative cuttings were taken from the initial selection in June of 1981 in a controlled environment in Salinas, Calif. by a technician working under formulations established and supervised by William E. Duffett.

Horticultural examination of controlled flowerings of successive plantings has shown that the unique combination of characteristics as herein disclosed for Calvex are firmly fixed and are retained through successive generations of asexual reproduction.

Calvex has not been observed under all possible environmental conditions. The phenotype may vary significantly with variations in environment such as temperature, light intensity and day length. The observations, measurements and comparisons describe plants grown in Salinas, Calif. and Bogota, Colombia under greenhouse conditions which approximate those generally used in commercial greenhouse practice.

The following traits have been repeatedly observed and are determined to be basic characteristics of Calvex which, in combination, distinguish this Chrysanthemum as a new and distinct cultivar:

(1) Flat capitulum form.
(2) Decorative capitulum type.
(3) Greyed-orange ray floret color.
(4) Diameter across face of capitulum up to 9 cm at maturity.

(5) Uniform nine to ten week photoperiodic flowering response to short days.
(6) Peduncle length ranging from 20 to 25 cm.
(7) Tall plant height, requiring one long day week prior to short days to attain a flowered plant height of 100 to 110 cm for year around flowering.
(8) Low temperature tolerance of 13° C. for initiation and development when grown in single stem cut spray programs with a continuous dark period of 12 to 13 hours.

The accompanying photographic drawings depict typical leaf and inflorescence characteristics of Calvex, with the color being as nearly true as possible with illustrations of this type.

Sheet 1 is a color photograph of Calvex grown as a single stem cut spray.

Sheet 2 is a black and white photograph of three views of the inflorescence of Calvex.

Sheet 3 is a black and white photograph showing the upper and under sides of the leaves of Calvex at three stages of development (mature, intermediate and immature).

Of the commercial cultivars known to the inventor, the most similar in comparison to Calvex is Flame Belair, disclosed in U.S. Plant Pat. No. 3,353. Reference is made to attached Chart A, which compares certain characteristics of Calvex to the same characteristics of Flame Belair.

Similar traits are type, color, form, diameter of capitulum, and plant height. Calvex has shorter peduncles, one week slower response, and superior tolerance of low temperatures for bud initiation and development.

In the following description, color references are made to The Royal Horticultural Society Colour Chart. The exact colors for corolla of ray florets are not precisely represented in The Royal Horticultural Society Colour Chart (RHS), and the colors given are the closest values to the actual color of Calvex. The color values were determined on plant material grown in Salinas, Calif. on July 19, 1985.

Classification:

*Botanical.*—*Dentrenthema morifolium*, Ramat., cv Calvex.

*Commercial.*—Decorative cut spray mum.

I. INFLORESCENCE

A. Capitulum:

*Form.*—Flat.

*Type.*—Decorative.

*Diameter across face.*—Up to 9 cm at maturity.

B. Corolla of ray florets:

*Color (general tonality from a distance of three meters).*—Greyed-orange.

*Color (upper surface).*—169B to 169C.

*Color (under surface).*—163B to 163C.

*Shape.*—Oblong.

C. Corolla of disc florets:

*Color (mature).*—3A.

*Color (immature).*—154B.

D. Reproductive organs:

*Androecium.*—Present disc florets only; scant pollen.

*Gynoecium.*—Present both ray and disc florets.

II. PLANT

A. General appearance:

*Height.*—Tall; 100 to 110 cm as a flowering plant from a rooted cutting with seven long days for year around flowerings maintaining a continuous dark period of 12 to 13 hours.

B. Foliage:

*Color (upper surface).*—147A.

*Color (under surface).*—147B.

*Shape.*—Wide, deep lobes; sharply serrated.

CHART A

COMPARISON OF CALVEX AND FLAME BELAIR

CHART A-continued

COMPARISON OF CALVEX AND FLAME BELAIR

| CULTIVAR | RAY FLORET COLOR | CAPITULUM FORM AND TYPE | SPRAY FORMATION | DIAMETER ACROSS FACE OF CAPITULUM |
|---|---|---|---|---|
| CALVEX | GREYED-ORANGE | FLAT DECORATIVE | 20 to 25 cm. PEDUNCLES | UP TO 9 cm. |
| FLAME | ORANGE-BRONZE | FLAT DECORATIVE | 15 to 22 cm. PEDUNCLES | UP TO 9 cm. |

| CULTIVAR | PLANT HEIGHT | FLOWERING RESPONSE PERIOD | TOLERANCE OF 13° C. |
|---|---|---|---|
| CALVEX | 100 to 110 cm. | NINE TO TEN WEEKS | GOOD, UNIFORM |
| FLAME | 80 to 90 cm. | NINE WEEKS | POOR, UNEVEN |

COMPARISONS MADE OF PLANTS GROWN AS SINGLE STEM CUT SPRAY MUMS WITH SEVEN LONG DAYS IN BOGOTA, COLOMBIA

I claim:

1. A new and distinct Chrysanthemum plant named Calvex, as described and illustrated, and particularly characterized as to uniqueness by the combined characteristics of flat capitulum form; decorative capitulum type; greyed-orange ray floret color; diameter across face of capitulum of up to 9 cm at maturity; uniform nine to ten week photoperiodic flowering response to short days; tall plant height when grown single stem; 20 to 25 cm peduncles on open, normally terminal sprays; and 13° C. minimum temperature tolerance for initiation and development of flowering buds.

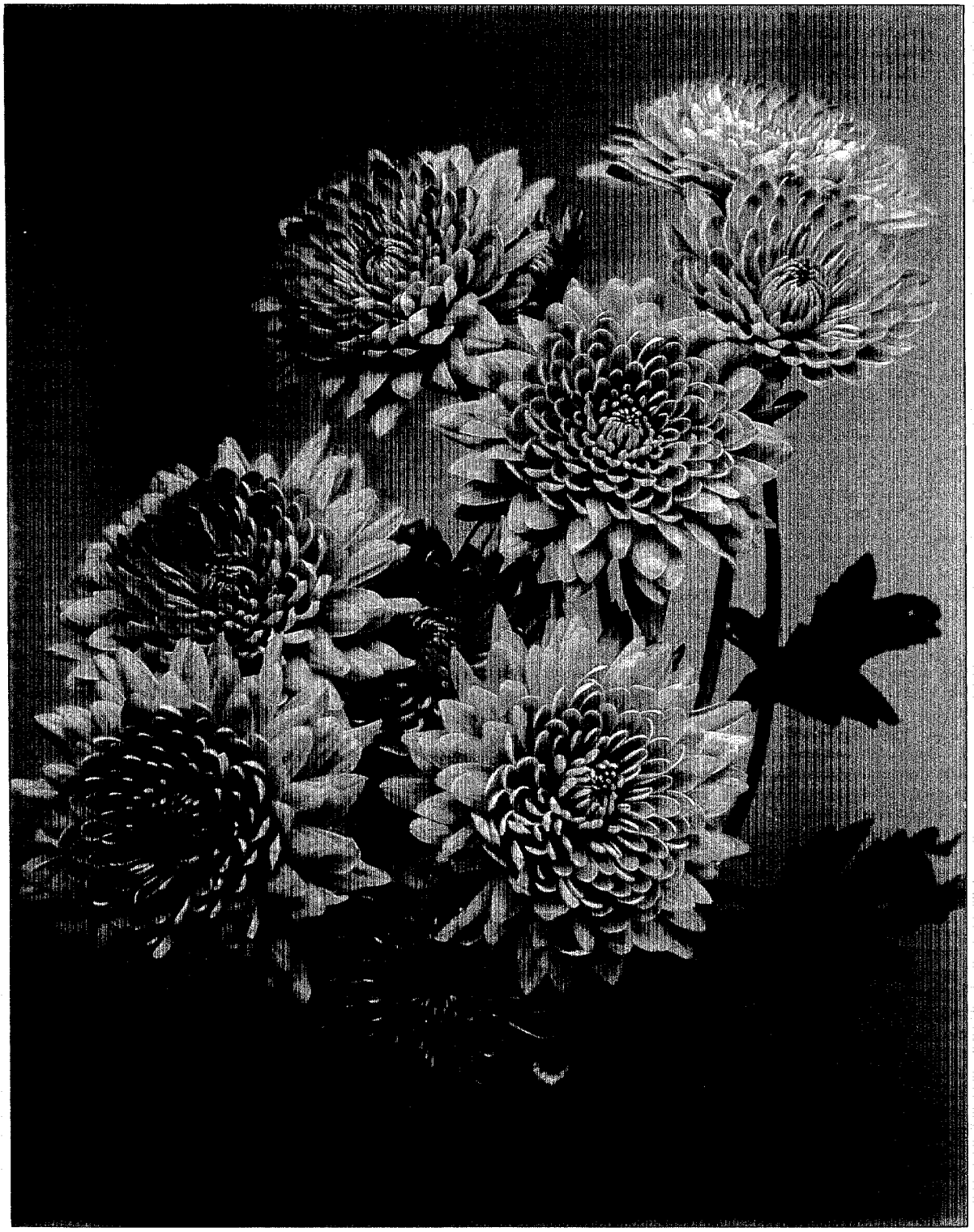

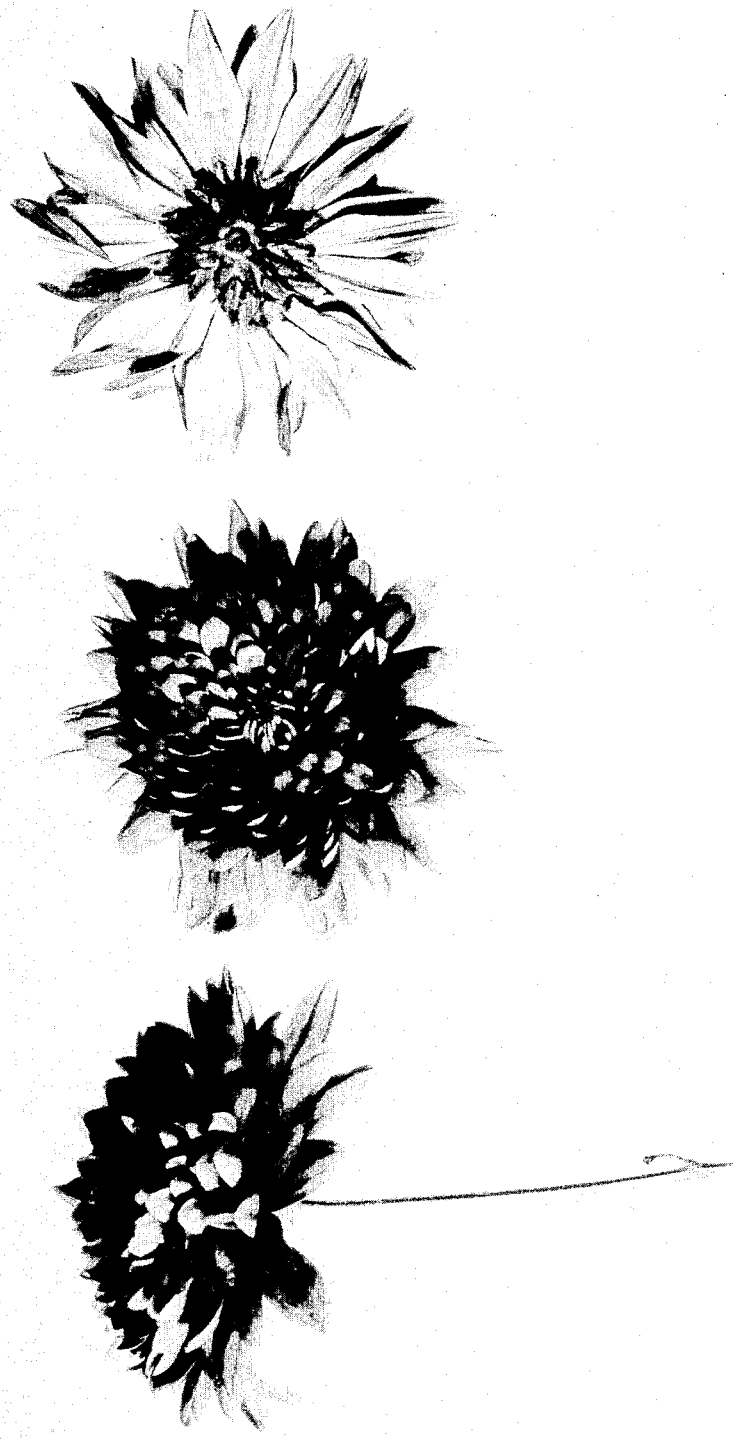

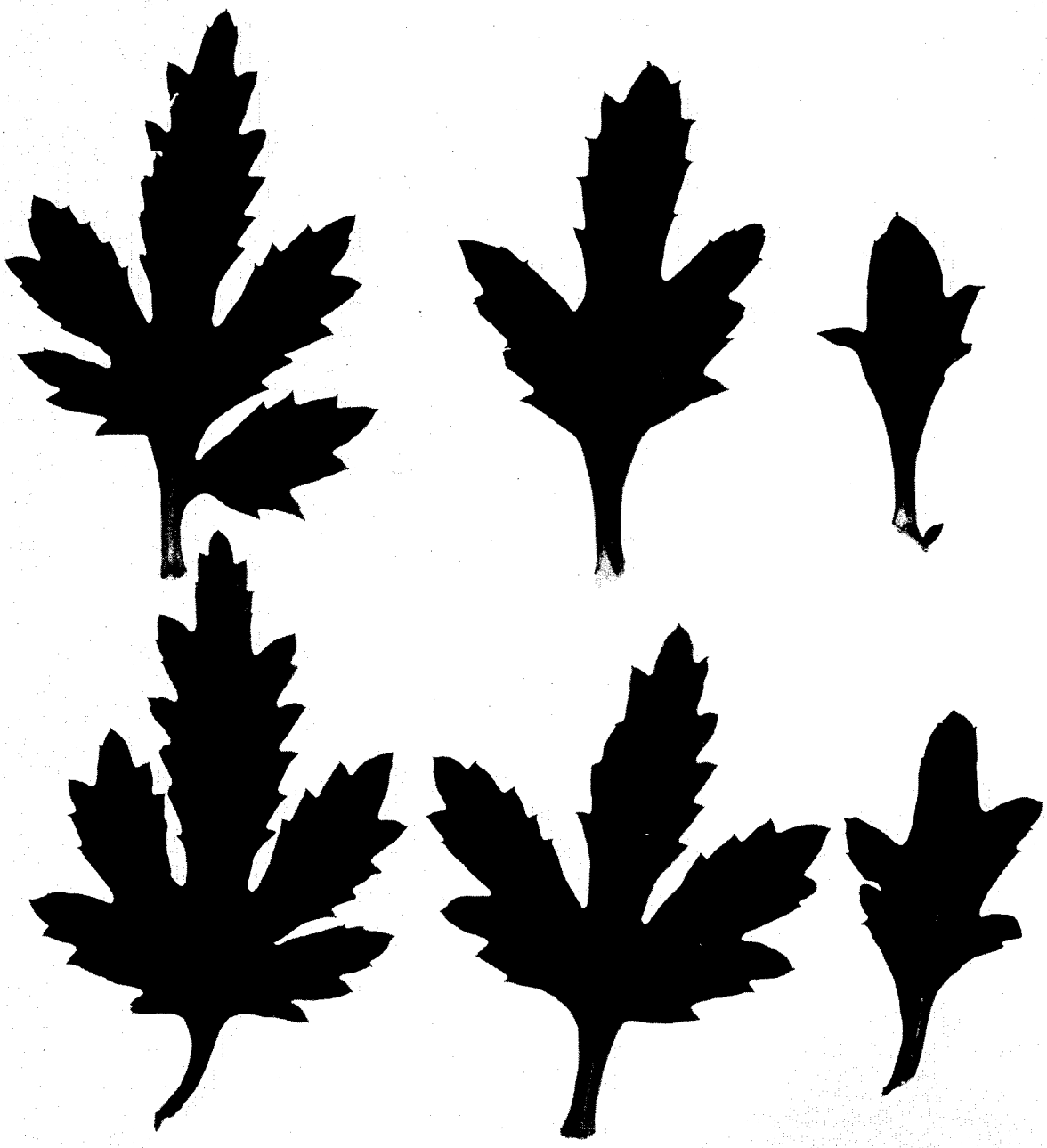

* * * * *